United States Patent [19]

Eichenbaum

[11] Patent Number: 4,694,828

[45] Date of Patent: Sep. 22, 1987

[54] LASER SYSTEM FOR INTRAOCULAR TISSUE REMOVAL

[76] Inventor: Daniel M. Eichenbaum, 5258 Linton Blvd., Suite 302, Delray Beach, Fla. 33445

[21] Appl. No.: 854,134

[22] Filed: Apr. 21, 1986

[51] Int. Cl.$^4$ ............................................. A61B 17/36
[52] U.S. Cl. .................................................. 128/303.1
[58] Field of Search ....................................... 128/4–8, 128/303.1, 395–398

[56] References Cited

U.S. PATENT DOCUMENTS

| | | | |
|---|---|---|---|
| 3,821,510 | 6/1974 | Muncheryan | 128/395 |
| 3,843,865 | 10/1974 | Nath | 128/395 |
| 3,858,577 | 1/1975 | Bass et al. | 128/6 |
| 3,865,113 | 2/1975 | Sharon et al. | 128/303.1 |
| 3,982,541 | 9/1976 | L'Esperance, Jr. | 128/303.1 |
| 4,122,853 | 10/1978 | Smith | 128/303.1 |
| 4,266,547 | 5/1981 | Kamiya | 128/303.1 |
| 4,273,109 | 6/1981 | Enderby | 128/6 |
| 4,369,785 | 1/1983 | Rehkopf et al. | 128/276 |
| 4,377,897 | 3/1983 | Eichenbaum et al. | 29/516 |
| 4,386,927 | 6/1983 | Eichenbaum | 604/51 |
| 4,433,692 | 2/1984 | Baba | 128/6 |
| 4,517,974 | 5/1985 | Tanner | 128/303.1 |
| 4,526,170 | 7/1985 | Tanner | 128/398 |
| 4,537,193 | 8/1985 | Tanner | 128/303.1 |
| 4,551,129 | 11/1985 | Coleman et al. | 128/303.1 |
| 4,564,011 | 1/1986 | Goldman | 128/303.1 |
| 4,608,980 | 9/1986 | Aihara | 128/303.1 |

FOREIGN PATENT DOCUMENTS

| | | | |
|---|---|---|---|
| 0033958 | 8/1981 | European Pat. Off. | 128/303.1 |
| 0172490 | 2/1986 | European Pat. Off. | 128/303.1 |
| 3209444 | 10/1982 | Fed. Rep. of Germany | 128/303.1 |

*Primary Examiner*—William E. Kamm
*Assistant Examiner*—Max F. Hindenburg
*Attorney, Agent, or Firm*—Roylance, Abrams, Berdo & Goodman

[57] ABSTRACT

A laser system for intraocular tissue removal including a handpiece and a nose cone assembly releasably coupled to the handpiece. The handpiece and nose cone assembly have mating passageways for aspiration and irrigation, and the handpiece supports a laser energy transmitting tube that is releasably received in the nose cone assembly. The nose cone assembly comprises an outer housing, an inner housing located inside the outer housing, and an aspiration tube located inside the inner housing. The outer and inner housings and the aspiration tube have coaxially aligned lateral openings defining a photovaporization chamber. The distal end of the laser energy transmitting tube is located adjacent the photovaporization chamber. In use, tissue to be removed is aspirated into the photovaporization chamber where it is vaporized by the laser energy and then conducted along the aspiration tube. Irrigation fluid flows between the outer and inner housings and then out the end of the outer housing to cool the photovaporization chamber and replace the tissue volume removed from the eye. Preferably, the laser energy transmitting means is a fiber optic rod with a lens fused on the end to direct the laser energy into the photovaporization chamber and thus prevent it from being scattered into the eye. Nose cone assemblies of different configurations can be releasably coupled to the handpiece and exchanged during surgery.

20 Claims, 9 Drawing Figures

LASER SYSTEM FOR INTRAOCULAR TISSUE REMOVAL

FIELD OF THE INVENTION

This invention relates generally to the field of laser instruments, and, more particularly, to an apparatus that uses laser energy to remove ocular tissue.

BACKGROUND OF THE INVENTION

It is well established in current ophthalmic literature that extracapsular cataract surgery is the preferred method of cataract removal. A crude form of extracapsular surgery was performed in the nineteenth century but was abandoned in favor of intracapsular cataract surgery in the first half of the twentieth century. Two factors, however, led to the rebirth of the extracapsular technique for cataract removal in the early 1970's.

The first factor was the development of the operating microscope with coaxial illumination. The second factor was the development of machinery to provide simultaneous irrigation and aspiration for use in a closed-eye microsurgical system along with instrumentation adequate to perform this task. Such instrumentation is disclosed in U.S. Pat. Nos. 4,386,927 and 4,377,897 to Eichenbaum, and 4,369,785 to Rehkopf et al, the disclosure of which are incorporated herein by reference.

Vitreous surgery requires irrigation-aspiration equipment that includes some form of knife blade to cut the vitreous strands, all performed through a 3 mm incision in the pars plana. These cutting devices are also used for lens removal through the pars plana or limbus when necessary. It is, therefore, natural to search for a cataract removal technique that would allow routine cataract removal through an equally small incision. While cortical material can be easily aspirated, a means must be used to break up the harder lens nucleus.

One early device having such means was the phacoemulsification system which introduced an ultrasonically driven, vibrating needle as a means of breaking up the hard lens nucleus, allowing cataract removal through a 3 mm incision in the limbus. The phacoemulsifier along with the two above-mentioned factors spearheaded the move toward extracapsular surgery. After an initial growth in phacoemulsification, however, use of the technique leveled off and it is now used by a relatively small group of surgeons for several reasons.

First, the technique is difficult to perform, requiring a skill level greater than that achieved by the majority of surgeons. Second, currently available equipment can damage adjacent intraocular structures due to heat and vibration of the ultrasonic needle. Finally, the necessity of enlarging the incision to accommodate intraocular lens implants eliminates the advantage of a 3 mm incision.

Recognizing the advantages of extracapsular cataract surgery, therefore, the majority of ophthalmic surgeons began to perform extracapsular surgery by expressing the intact nucleus and using irrigation-aspiration equipment only to remove the cortex. Most surgeons do not feel comfortable trying to hold and control a bulky phacoemulsifier handpiece on the end of which sits an exposed needle vibrating in the confined space of the anterior chamber.

Recently, the use of lasers to perform eye surgery has also increased, as evidenced by the growing number of patents disclosing such use. Among these are U.S. Pat. Nos. 4,517,974 and 4,537,193 to Tanner; 4,564,011 to Goldman; 4,273,109 to Enderby; 4,122,853 to Smith; 3,982,541 to L'Esperance, Jr.; 3,865,113 to Sharon et al; 3,858,577 to Bass et al; 3,843,865 to Nath; 3,821,510 to Muncheryan; German Pat. No. 3,209,444 to Renz; and published European Patent Application No. 33,958 to Atsumi et al. Thus, it is logical to expect that the ultrasonic vibrating needle of the phacoemulsification system would give way to the current trend of using lasers. However, to date no acceptable laser surgical devices have been developed for use in extracapsular cataract surgery. The lack of such surgical devices reflects the difficult task of satisfying the required design parameters. Such parameters require an instrument to be: (1) capable of operating through a small incision; (2) able to direct the fragmenting energy directly and accurately to a very small area; (3) capable of preventing random laser or heat energy from damaging adjacent areas of the eye during an operation; and (4) configured to provide a sufficiently large opening to accommodate large, hard pieces of lens, while at the same time preventing unacceptably high levels of aspiration.

Additionally, due to the extremely high expense of such surgical equipment, it is greatly desirable to have a laser surgical system which can facilitate other types of laser surgery such as vitreous surgery. Thus, not only must the above parameters be satisfied, but the system must be designed to be as versatile as possible. This is especially true when different types of ocular surgery must be performed during a single operation. In such situations, the surgeon must be able to quickly and easily switch back and forth between different types of surgical instruments.

SUMMARY OF THE INVENTION

Accordingly, it is an object of this invention to provide a laser surgical device which is capable of operating through a small incision.

A second object of this invention is to provide a laser surgical device able to direct the fragmenting laser energy directly and accurately to a very small area.

Another object of this invention is to provide a laser surgical device capable of preventing random laser or heat energy from damaging adjacent areas of the eye during surgery.

Another object of this invention is to provide a laser surgical device configured to provide a sufficiently large opening to accommodate large, hard pieces of lens, while at the same time preventing unacceptably high levels of aspiration.

Yet another object of this invention is to provide a laser surgical system which can facilitate not only cataract surgery, but other types of laser surgery as well.

The foregoing objects are basically attained by a needle probe for removing ocular tissue comprising an outer housing having first and second ends and inner and outer surfaces, said outer housing having a first aperture on a first side of said housing adjacent said second end, and a second aperture substantially at said second end; an inner housing located inside said outer housing, said inner housing having first and second ends, first and second opposite sides, and inner and outer surfaces, said inner housing having an aperture positioned substantially coaxially with said first aperture in said outer housing, and on said first side of said inner housing, which side is laterally adjacent to said first side of said outer housing; said coaxial apertures in said outer and inner housings defining a photovaporization chamber; said inner surface of said outer housing and said outer surface of said inner housing defining an irrigation passageway for irrigating liquid, which liquid flows through said passageway from said first ends of said outer and inner housings and exits the probe through said second aperture in said outer housing, said irrigation passageway being connectable to an irrigation generator; a laser tube positioned inside said inner housing and laterally adjacent to said first side of said inner housing, said laser tube having first and second ends, said first end being connectable to a laser generator and said second end being located adjacent said photovaporization chamber to deliver laser energy into said chamber; and an aspiration tube having first and second ends, and first and second opposite sides, said aspiration tube being positioned inside said inner housing with said second side of said aspiration tube being laterally adjacent to said second side of said inner housing, said aspiration tube having an aperture on said first side of said aspiration tube adjacent said second end, said aperture being positioned substantially coaxially with said first aperture of said outer housing and said aperture of said inner housing, said first end of said aspiration tube being connectable to an aspiration generator.

In another embodiment of this invention, the needle probe comprises a handpiece having passageways for aspiration, irrigation, and laser energy, and a nose cone assembly having passageways for aspiration, irrigation, and laser energy. Several different types of nose cone assemblies can be used with the handpiece and are releasably engageable therewith.

Other objects, advantages and salient features of the present invention will become apparent from the following detailed description, which, taken in conjunction with the annexed drawings, discloses preferred embodiments of the invention.

BRIEF DESCRIPTION OF THE DRAWINGS

Referring now to the drawings which form a part of this original disclosure.

DETAILED DESCRIPTION OF THE INVENTION

Figure 1:
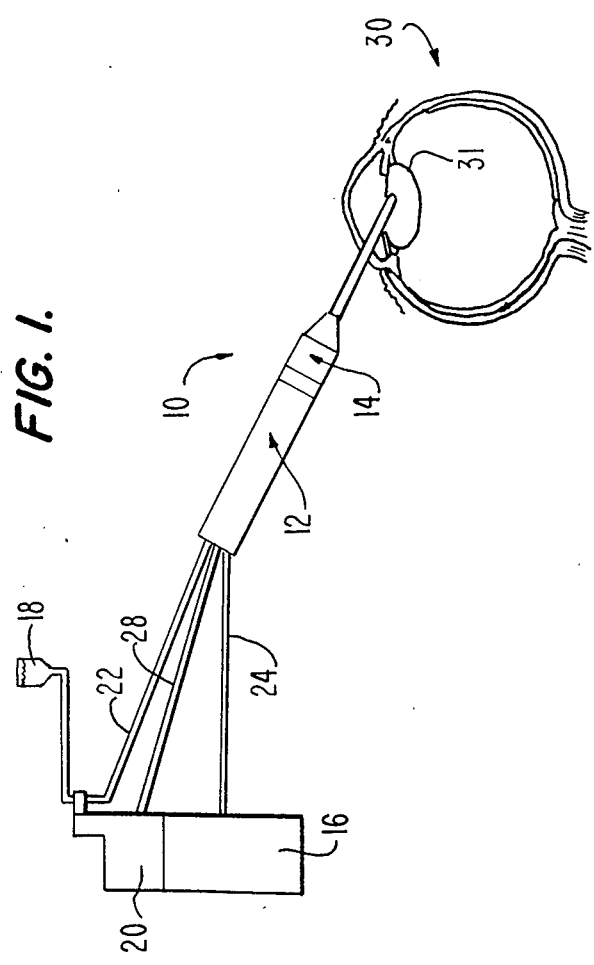
FIG. 1 is a schematic illustration of a laser surgical device in accordance with this invention.

Referring now to FIG. 1, needle probe 10 is shown comprising handpiece 12 and nose cone assembly 14. The handpiece 12 is attached to laser energy generator 20, aspiration generator 16, and irrigation generator 18, by laser transmitting means 28, aspiration transmitting means 24, and irrigation transmitting means 22, respectively. Generators 20, 16 and 18 are conventional, and transmitting means 28, 24 and 22 are preferably flexible tubing. The probe is intended for use on eye 30 and lens 31.

Figure 2:
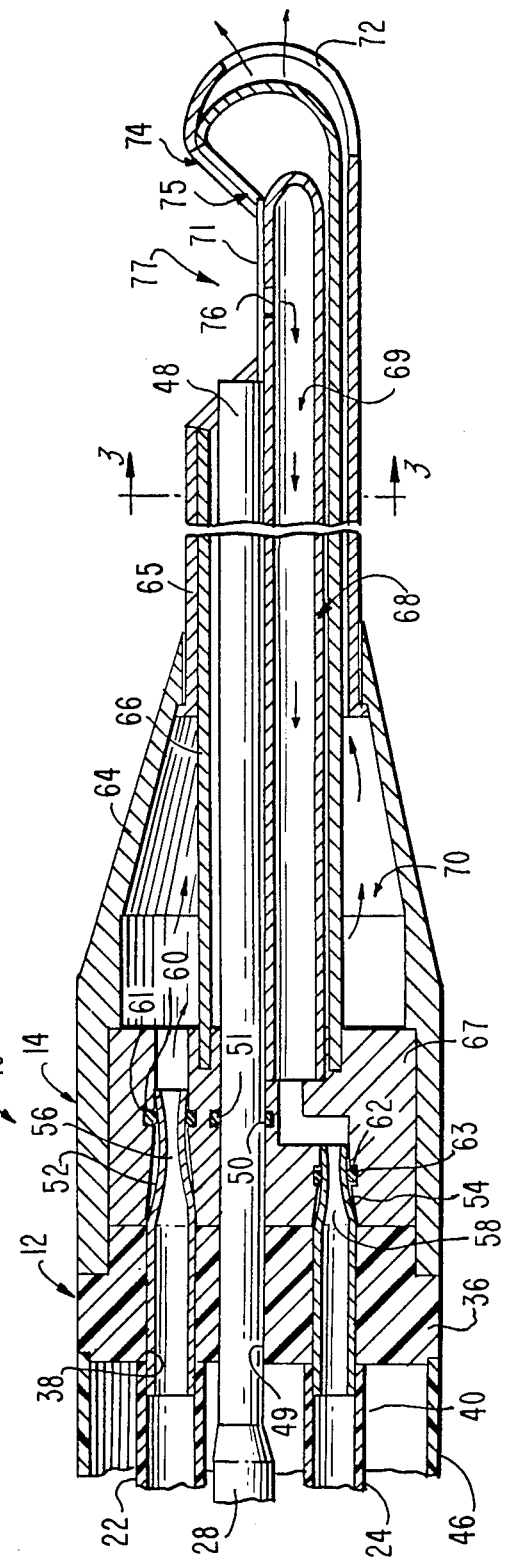
FIG. 2 is a longitudinal cross-sectional view of a needle probe in accordance with this invention, which probe is configured for cataract surgery.
Figure 9:
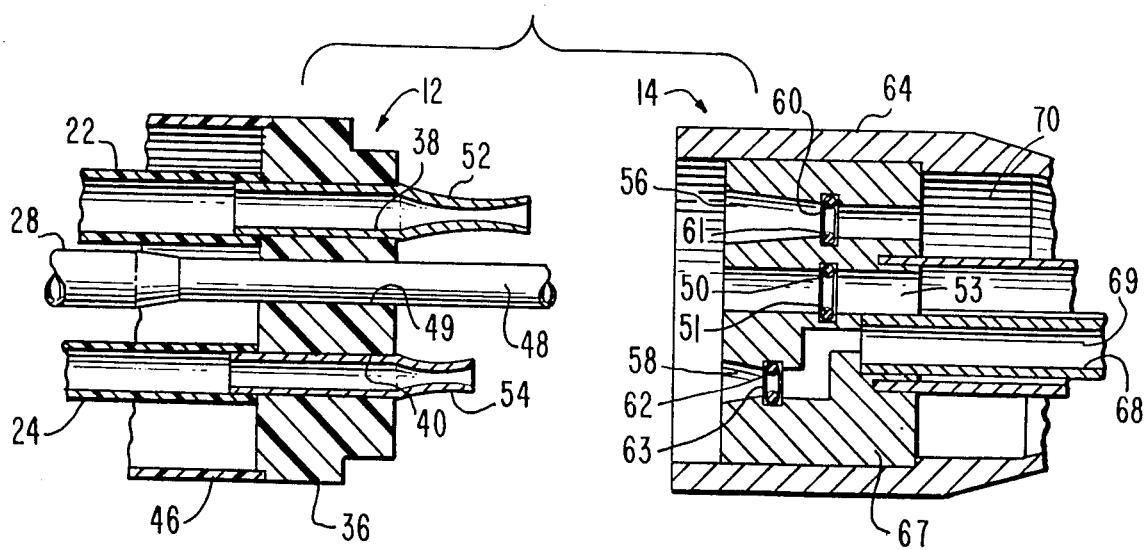
FIG. 9 is a longitudinal cross-sectional view of the mating sections of the needle probe shown in FIG. 2.

As seen in FIGS. 2 and 9, needle probe 10 has handpiece 12 releasably coupled to nose cone assembly 14. The handpiece 12 comprises disk 36 having internal passageways 38 and 40 for irrigation and aspiration, respectively, which rigidly receive tubular male members 52 and 54 therein. Irrigation transmitting means 22 and aspiration transmitting means 24 are attached to disk 36 via male members 52 and 54, and transmit irrigation and aspiration via male members 52 and 54, respectively. An outer cylindrical wall 46 is rigidly attached to disk 36. Laser tube 48 is coupled to laser transmitting means 28 and passes through a central throughbore 49 in disk 36, a central throughbore 53 (shown in FIG. 9) in the nose cone assembly 14, and is secured in place by an O-ring 50 in recess 51. Male mating members 52 and 54 rigidly affixed to the handpiece are releasably coupled in female receptacles 56 and 58 in the nose cone assembly by O-rings 60 and 62, which are positioned in recesses 61 and 63, respectively.

The nose cone assembly 14 is comprised of inner tubular housing 66, aspiration tube 68, and an outer tubular housing 65, which is received in tubular base 64 having a support disk 67 therein. Passageway 70, which is defined by the inner surfaces of the tubular base 64 and inner housing 65, and the outer surface of the inner housing 66, provides an area for flow of irrigating liquid along the outer surface of the inner housing 66. After flowing through passageway 70, the irrigating liquid exits through the slot-shaped aperture 72 in the distal end of the outer housing 65. This flow of irrigating liquid removes any excess heat from the nose cone assembly that might otherwise be transmitted to adjacent ocular areas. Apertures 74 and 75 represent the apertures respectively in the outer housing 65 and the inner housing 66. Aperture 76 is provided in the aspiration chamber. These apertures are aligned on the same lateral sides of the outer and inner housings and the aspiration tube, are substantially coaxial, and define a photovaporization chamber on zone 77 with the bottom thereof being provided by aspiration tube 68.

Except for the male members, the handpiece 12 is shown as being constructed of a plastic, but can be constructed of other materials including sterilizable metals such a stainless steel. The handpiece can be disposable or nondisposable, but is preferably disposable, and therefore, made of plastic.

The irrigation transmitting means 22 and aspiration transmitting means 24 are shown essentially as tubular conduits, but can comprise any means capable of transmitting irrigation and aspiration.

The male mating members 52 and 54 can comprise any material capable of securing handpiece 12 to nose cone assembly 14. Such materials include plastics and metals, with the preferred material being stainless steel.

Likewise, the laser tube 48 can be comprised of various materials including plastics and metals. The laser tube 48 houses a laser transmitting means such as an optical fiber. A suitable configuration for fiber optic transmission of laser energy is discussed in greater detail with reference to FIG. 8.

The nose cone assembly 14 is shown as being constructed of a metal, which is advantageously stainless steel. Stainless steel is advantageous because it can be configured to very fine tolerances, and sterilized using known procedures. However, it is contemplated that the nose cone assembly could also be made of plastic or other materials. If the nose cone assembly is comprised of a metal such as stainless steel, it will generally be regarded as nondisposable.

The O-rings 50, 60 and 62 are shown as being comprised of rubber, but can also be comprised of metal or plastic. It is contemplated that other types of securing means such as locking rings can be used to secure the male members within the female receptacles.

Figure 3:
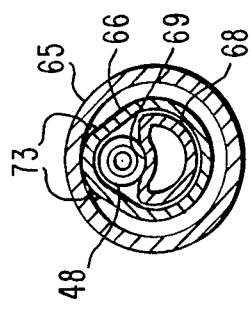
FIG. 3 is a cross-sectional view taken along line 3—3 in FIG. 2.

FIG. 3 is a cross-sectional view of FIG. 2 taken along line 3—3, and shows the relationship and configuration of the various components of the needle probe. The outer housing 65 and laser tube 48 have substantially circular cross sections. The aspiration tube 68 has a substantially semi-circular cross section with a longitudinal concave groove 71 in its flat top and the inner housing 66 has a substantially pear-shaped cross section, although it could be circular.

The aspiration tube can be of any configuration but advantageously is configured to act as a guide or support for the laser tube. Thus, laser tube 48 is received in groove 71 as seen in FIG. 3 to support it and maintain its alignment. Likewise, the inner housing 66, which is shown with an irregularly shaped cross section, can act as a guide or support for the laser tube by engaging it to insure correct positioning. However, other cross-sectional configurations for the outer and inner housings, laser tube and aspiration tube are certainly contemplated. If possible, such designs should insure correct positioning of the laser tube so that its distal end is adjacent the photovaporization chamber 77 as seen in FIG. 2.

As seen in FIG. 3, the upper side of the inner housing 66 engages the upper side of the outer housing 65 and solder 73 couples these housings together.

While the dimensions of a needle probe for cataract surgery can vary slightly and still be within the scope of this invention, the following dimensions have been found to be advantageous.

TABLE 1

| Part | Inside Diameter (mm) | Outside Diameter (mm) |
|---|---|---|
| Outer Housing | 1.5–1.70 | 1.65–1.82 |
| Inner Housing | 1.12 | 1.27 |
| Laser Tube | 0.305 | 0.508 |

The apertures 74 and 75 in the outer and inner housings, which accommodate entry of the hard lens material into the photovaporization chamber, are advantageously oval and of substantially the same dimensions. It has been found that satisfactory results are obtained with a probe having oval apertures in the outer and inner housings aout 2.5 mm long, about 1.0 mm wide at their widest sections, and about 0.7 mm deep at their deepest sections. The aspiration tube aperture is circular and is about 0.3 mm–0.4 mm in diameter. Satisfactory results have been obtained using a nose cone assembly having an overall length of about 48 mm and a needle section length of about 22 mm.

The aspiration aperture is kept smaller than the outer and inner housing apertures to prevent high levels of aspiration which would tend to collapse the eye. Yet the outer and inner housing apertures are relatively larger to allow large pieces of the ocular tissue to be drawn into the photovaporization chamber 77.

Advantageously, the rims of oval apertures 74 and 75 are soldered together to prevent irrigation fluid from exiting therefrom.

During cataract surgery, the needle probe 10 of this invention is brought into contact with the hard lens material of the cataract. Aspiration draws the large, hard lens material into the photovaporization chamber 77 where it is fragmented by laser energy and aspirated. The irrigation passageway provides clear saline solution to replace the tissue removed, volume for volume. Additionally, the irrigating liquid removes excess heat from the probe, thereby preventing damage to adjacent ocular areas.

Figure 4:
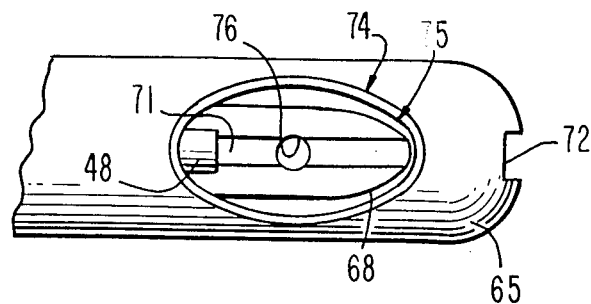
FIG. 4 is a top plan view of the needle probe of FIG. 2.

FIG. 4 is a top view of the needle section of the nose cone assembly of FIG. 2. The specific relationships among the tip of the laser tube 48, the aspiration tube 68, and apertures 74 and 76 can be seen most clearly.

FIG. 9 provides a clear cross-sectional view of the mating areas of hand piece 12 and nose cone assembly 14. In this figure, throughbore 49 in disk 36, and throughbore 53 in nose cone assembly 14 can more clearly be seen. Also, the male mating members 52 and 54, which extend axially outward from the handpiece, as well as the female receptacles 56 and 58, which extend axially within the nose cone assembly, are more readily apparent.

It is contemplated, of course, that the male members can be on either of the mating pieces, or, for example, the handpiece 12 could have one male member and the nose cone assembly 14 could have one male member, with each member having correspondingly coupling female receptacles.

Figure 5:
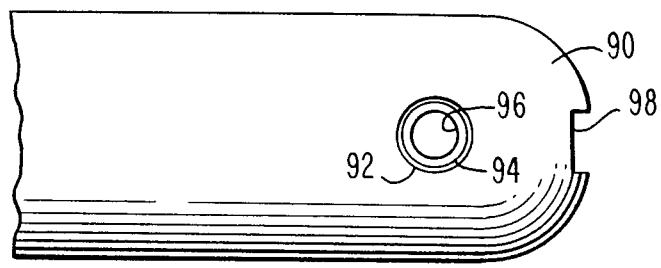
FIG. 5 is a top plan view of a second embodiment of a needle probe in accordance with this invention, which probe is configured for vitreous removal.

FIG. 5 is a top view of a slightly modified needle section of a nose cone assembly designed for vitreous surgery. It can be seen that the outer housing aperture 92, and inner housing aperture 94 are significantly smaller than those required for cataract surgery as discussed above. This is because vitreous tissue is more elastic and can be easily aspirated into a smaller aperture. The aspiration aperture 96 is approximately the same size as required for cataract surgery, i.e., 0.3 mm. The outer housing aperture for vitreous removal can be about 0.4 mm in diameter. Similar but somewhat smaller dimensions for the inner housing aperture are acceptable.

Figure 6:
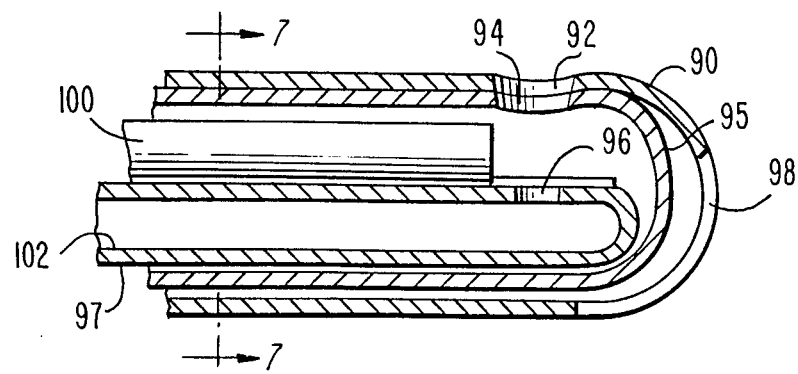
FIG. 6 is longitudinal cross-sectional view of the needle probe of FIG. 5.

FIG. 6 is a longitudinal cross-sectional view of the needle probe shown in FIG. 5. Aperture 92 in outer housing 90 is substantially coaxially aligned with apertures 94 and 96. Slot-like aperture 98 is located substantially on the end of the outer housing 90 and allows irrigating liquid to exit the needle probe.

Figure 7:
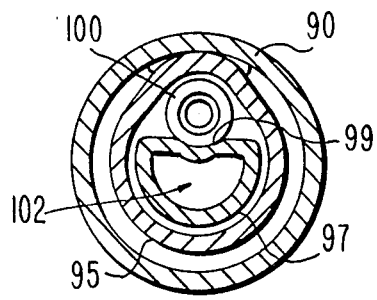
FIG. 7 is a cross-sectional view taken along line 7—7 in FIG. 6.

FIG. 7 is a cross-sectional view of the needle probe shown in FIG. 6 taken along line 7—7. The configuration of the outer housing 90, inner housing 95, aspiration tube 97, and laser tube 100 are substantially as shown in FIG. 3, including groove 99 in the upper surface of the aspiration tube 97 receiving laser tube 100 therein.

In vitreous surgery, the vitreous probe functions substantially as does the cataract probe. Vitreous is drawn into a photovaporization chamber located between apertures 92, 94 and 96 by aspiration, where it is fragmented by laser energy and removed through the aspiration passageway 102. Irrigating liquid then replaces the tissue removed, volume for volume.

Figure 8:
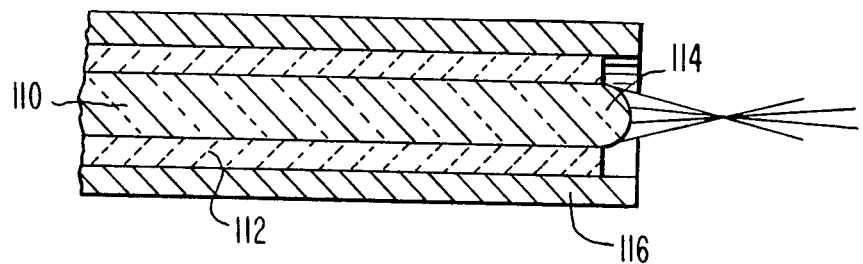
FIG. 8 is a longitudinal cross-sectional view of fiber optic means for transmitting laser energy, which means can be used in accordance with this invention.

FIG. 8 illustrates laser transmitting means which can be used in accordance with this invention. The laser transmitting means comprises optical fiber 110 encased in cladding 112. A lens 114 is fused to the distal end of the optical fiber to focus the laser energy that is transmitted. The optical fiber and cladding are housed in laser tube 116.

The diameter of the optical fiber can vary but it has been found that a 200 micron diameter quartz fiber will provide satisfactory results. The cladding comprises a material that will both protect the optical fiber from damage and prevent the loss of laser energy along the length of the fiber. Suitable claddings can comprise silicon quartz, plastic, etc. This invention contemplates the presence of one optical fiber within the laser tube but it can simultaneously transmit laser energy of different wavelengths.

This invention, as described above, provides significant advantages not afforded by prior art laser surgical devices. One advantage is its ability to safely perform cataract surgery without damaging adjacent ocular areas. This is due, in part, to the design of the laser delivery system, which controls and confines the laser energy within the irrigation-aspiration tip and the photovaporization chamber. Such confinement of the laser delivery system insures that random laser energy will not escape the probe to damage adjacent ocular areas. The design further enhances safety because the laser transmitting means is substantially centrally located within the probe. A passageway is provided between the inner and outer housings, where flowing irrigation fluid acts as a coolant to prevent heat buildup from the laser. Such buildup could also cause significant damage to adjacent ocular areas.

A second advantage is that the design of the photovaporization chamber allows large, hard pieces of lens to be brought into contact with laser energy where they can be fragmented and aspirated. The position and size of the aspiration aperture, which is at the bottom of the photovaporization chamber, insures that the adjacent ocular tissue will not be subjected to a dangerous amount of aspiration.

Finally, the use of mating handpiece and nose cone assembly renders the system versatile and useful for other types of ocular surgery. This is especially true when more than one type of ocular tissue must be removed in the course of a single operation and variously configured nose cone assemblies can be used.

Thus, the unique combination of features possessed by the needle probes of this invention render them uniquely suited for cataract and other types of ocular surgery.

While several advantageous embodiments have been chosen to illustrate the invention, it will be understood by those skilled in the art that various changes and modifications can be made therein without departing from the scope of the invention as defined in the appended claims.

What is claimed is:

1. A needle probe for removing tissue comprising:
an outer housing having first and second ends and inner and outer surfaces, said outer housing having means defining a first aperture on a first side of said housing adjacent said second end, and means defining a second aperture substantially at said second end;
an inner housing located inside said outer housing, said inner housing having first and second ends, first and second opposite sides, and inner and outer surfaces, said inner housing having means defining an inner housing aperture positioned substantially coaxially with said means defining said first aperture in said outer housing, and on said first side of said inner housing, which side is laterally adjacent to said first side of said outer housing;
the volume bounded by said means defining said coaxial first and inner housing apertures in said outer and inner housings defining a photovaporization zone;
said inner surface of said outer housing and said outer surface of said inner housing defining an irrigation passageway for irrigating liquid, which liquid flows through said passageway from said first ends of said outer and inner housings and exits the probe through said second aperture in said outer housing, said irrigation passageway being connectable to an irrigation generator;
a laser tube positioned inside said inner housing and laterally adjacent to said first side of said inner housing, said laser tube having first and second ends, said first end being connectable to a laser generator and said second end being located adjacent said photovaporization zone to deliver laser energy into said zone; and
an aspiration tube having first and second ends, and first and second opposite sides, said aspiration tube being positioned inside said inner housing with said second side of said aspiration tube being laterally adjacent to said second side of said inner housing, said aspiration tube having means defining an aspiration aperture on said first side of said aspiration tube adjacent said second end, said means defining said aspiration aperture being positioned substantially coaxially with said means defining said first aperture of said outer housing and said means defining said inner housing aperture of said inner housing, said first end of said aspiration tube being connectable to an aspiration generator.

2. The probe of claim 1, wherein
said laser tube includes fiber optic means adapted to transmit laser energy, said fiber optic means having a distal end, said distal end being in the proximity of said second end of said laser tube.

3. The probe of claim 2, wherein
said fiber optic means includes a lens at its distal end.

4. The probe of claim 3, wherein
said fiber optic means has a diameter of about 200 microns.

5. The probe of claim 1, wherein
said first side of said aspiration tube engages said laser tube.

6. The probe of claim 5, wherein
said first side of said aspiration tube has a groove therein recovering a portion of said laser tube therein.

7. The probe of claim 1, wherein
said first side of said aspiration tube forms the bottom of said photovaporization zone.

8. The probe of claim 1, wherein
said first aperture in said outer housing has a maximum length of about 2.5 mm and a maximum width of about 1.0 mm.

9. The probe of claim 8, wherein
said first aperture is oval.

10. The probe of claim 8, wherein
said aspiration aperture in said aspiration tube has a diameter of about 0.30 mm.

11. The probe of claim 8, wherein said outer housing has an outside diameter of about 1.65 mm;
said inner housing has an outside diameter of about 1.3 mm; and
said laser tube has an outside diameter of about 0.5 mm.

12. A needle probe for removing tissue comprising:
first and second members including
  a handpiece having an aspiration passageway, an irrigation passageway and a laser energy passageway, and
  a nose cone assembly having an aspiration passageway, an irrigation passageway, and a laser energy passageway; and
means for releasably coupling said first and second members, said means including at least one male member extending axially outward from said first member, and at least one correspondingly mating female receptacle extending axially within said second member, said male member being releasably coupled with said female receptacle,
said nose cone assembly including
  an outer housing having means defining a first lateral aperture spaced from its distal end and means defining an aperture at its distal end,
  an inner housing located inside said outer housing, having means defining a second lateral aperture coaxially aligned with said means defining said first lateral aperture, and being spaced from said outer housing to define said nose cone assembly irrigation passageway therebetween, and
  an aspiration tube located inside said inner housing, forming said nose cone assembly aspiration passageway, and having means defining a third lateral aperture coaxially aligned with said means defining said first and second lateral apertures,
the volume bounded by said coaxially aligned means for defining said first, second and third lateral apertures defining a photovaporization zone, said nose cone assembly laser energy passageway extending into said inner housing and having a distal end located adjacent said photovaporization zone.

13. The probe of claim 12, wherein
said handpiece is said first member, and has two male members extending axially outward from said aspiration passageway and said irrigation passageway.

14. The needle probe of claim 12, wherein,
said handpiece further includes laser transmitting means located in said laser energy passageway for transmitting laser energy, said laser transmitting means being releasably received in said laser energy passageway in said nose cone assembly.

15. The needle probe of claim 14, wherein
said laser transmitting means includes fiber optic means, said fiber optic means having a distal end.

16. The needle probe of claim 15, wherein
said fiber optic means includes a lens at its distal end.

17. The needle probe of claim 16, wherein
said fiber optic means is about 200 microns in diameter.

18. The needle probe of claim 14, and further comprising
an irrigation generator, an aspiration generator, and a laser energy generator;
means for connecting said irrigation generator and aspiration generator to said irrigation and aspiration passageways in said handpiece; and
means for connecting said laser energy generator to said laser transmitting means.

19. A needle probe for removing tissue comprising:
a handpiece having irrigation and aspiration passageways therein and a laser energy trasmitting optical fiber coupled thereto;
means for generating a vacuum coupled to said aspiration passageway;
means for generating irrigation fluid flow coupled to said irrigation passageway;
means for generating laser energy coupled to said optical fiber;
a nose cone assembly having irrigation and aspiration passageways; and
means for coupling said irrigation and aspiration passageways in said handpiece and in said nose cone assembly,
said nose cone assembly including
  an outer housing having means defining a first lateral aperture spaced from its distal end and means defining an aperture at its distal end,
  an inner housing located inside said outer housing, having means defining a second lateral aperture coaxially aligned with said means defining said first lateral aperture, and being spaced from said outer housing to define said irrigation passageway therebetween, and
  an aspiration tube located inside said inner housing, forming said aspiration passageway, and having means defining a third lateral aperture coaxially aligned with said means defining said first and second lateral apertures,
the volume bounded by said coaxially aligned means for defining said first, second and third lateral apertures defining a photovaporization zone therebetween, said optical fiber extending into said inner housing and having a distal end located adjacent said photovaporization zone.

20. The probe of claim 19, and further comprising
a lens located at said distal end of said optical fiber for focusing the laser energy into said photovaporization zone.

* * * * *